United States Patent [19]

Strobel

[11] 4,342,746

[45] * Aug. 3, 1982

[54] METHOD FOR TREATING DUTCH ELM DISEASE

[75] Inventor: Gary A. Strobel, Bozeman, Mont.

[73] Assignee: Endowment and Alumni Foundation at Montana State University, Bozeman, Mont.

[ * ] Notice: The portion of the term of this patent subsequent to Jul. 7, 1998, has been disclaimed.

[21] Appl. No.: 205,862

[22] Filed: Nov. 10, 1980

Related U.S. Application Data

[63] Continuation-in-part of Ser. No. 95,448, Nov. 19, 1979, Pat. No. 4,277,462.

[51] Int. Cl.$^3$ .................... A01N 63/00; A01N 63/02
[52] U.S. Cl. ................................ 424/93; 424/115; 435/170; 435/874
[58] Field of Search ............... 424/115, 93; 435/170, 435/874

[56] References Cited

U.S. PATENT DOCUMENTS 3,155,585 11/1964 De Vay .............................. 424/115

OTHER PUBLICATIONS

Myers et al., Proc. Amer. Phytopathol. Soc., vol. 12, (1978), p. 350.
Campana, Proc. Amer. Phytopathol. Soc., vol. 3, (1967), p. 266.
De Vay et al., Phytopathology, vol. 58, (1968), pp. 95-101 and vol. 52, (1962), p. 360.
Sinden et al., Physiol. Pl. Path., vol. 1, (1971), pp. 199-213.
Gross et al., J. Appt. Bact., vol. 43, (1977), pp. 453-463.
Gross et al., Phytopathology, vol. 67, (1977), pp. 475-483.
Annual Meeting of American Phytopathological Society, Aug. 1978; Tucson, Arizona (Oral Presentation) by D. F. Myers.
Minneapolis Star, Apr. 11, 1979, "Elm Disease Cure is Near, Experts Say".
Dick Gray, Passwords, Apr. 11, 1979.
Chemical Abstracts 92:16306q (Proc. Inst. Conf. Pathol. Bact., 4th 1978, 2, 643-650.
Chemical Abstracts, 88:84316k (Physiol. Plant Pathol. 1977, 11(1), 13-28).
Chemical Abstracts, 82:12522c (Antimicrob. Agents Chemother. 1974, 6(1), 76-83).
Chemical Abstracts 75:85365u (Physiol. Plant Pathol. 1971, 1(2), 199-213).

*Primary Examiner*—Richard Raymond
*Attorney, Agent, or Firm*—Lowe, King, Price & Becker

[57] ABSTRACT

A novel method for treating Dutch elm disease by use of a certain type of *P. syringae*. This method includes the step of applying this microorganism to an elm tree early in the growing season. Also disclosed is a process for isolating an antimycotic substance formed by an exemplary strain of this type of microorganism, and a process for isolating a high molecular weight antibiotic also formed by this exemplary strain. In addition, the high molecular weight antibiotic is disclosed, as well as methods for treating Dutch elm disease using either the high molecular weight antibiotic or the antimycotic substance.

20 Claims, No Drawings

METHOD FOR TREATING DUTCH ELM DISEASE

CROSS-REFERENCE TO RELATED APPLICATION

This application is a continuation-in-part application of a U.S. Patent Application Ser. No. 95,448, filed Nov. 19, 1979, now U.S. Pat. No. 4,277,462, issued July 7, 1981, and entitled "Method for Treating Dutch Elm Disease Using *P. Syringae*".

TECHNICAL FIELD

This invention related to the treatment of Dutch elm disease.

BACKGROUND

Dutch elm disease, caused by *Ceratocystis ulmi* (Buisman) C. Moreau, has killed millions of American elms since its first reported occurrence in the United States in 1930. The economic loss due to Dutch elm disease is estimated to be several billion dollars. Recommended control strategies for this disease have included destruction of vectors by sanitation and insecticide sprays, soil treatments to prevent root graft transmission, protective and therapeutic treatments with systemic fungicides, intensive surveillance and eradicative pruning, and resistant varieties of elm. While a single valuable tree might be protected by a combination of one or more of these strategies at a cost of several hundred dollars per year, no single control procedure has been completely effective.

Until recently, biological control of plant disease has been directed more towards root diseases than disease of aerial plant parts, such as Dutch elm disease. Nevertheless, biological control of *Fomes annosus* (Fr.) Cke in the stumps of Scots pine by a second basidiomycete, *Peniophora gigantea* (Fr.) Masse, is an example of a very successful biological control involving an aerial plant part. Biological control of Dutch elm disease has been directed at the elm bark beetle vector and at the saprophytic stage of *C. ulmi*.

It is known that certain strains of *Pseudomonas syringae* produce broad spectrum antibiotics that are effective on a number of pathogenic bacteria and fungi when tested in vitro. This type of art is illustrated by U.S. Pat. No. 3,155,585 to De Vay; J. E. De Vay et al, *Phytopathology*, 58: 95–101 (1968); S. L. Sinden et al, *Physiol. Plant Pathol.*, 1: 199–213 (1971); D. Gross and J. E. De Vay, *Proc. Amer. Phytopathol. Soc.* 3: 269–270 (1976); D. C. Gross et al, *J. Appl. Bact.*, 43: 453–463 (1977); J. E. De Vay and G. A. Strobel, *Phytopathology*, 52: 360 (1962); and D. C. Gross and J. E. De Vay, *Phytopathology*, 67: 475–483 (1977). U.S. Pat. No. 3,155,585 also shows an in vivo effect in certain fruit trees of the antibiotic material formed by *P. syringae*.

The use of nystatin, an antifungal agent to arrest Dutch elm disease in the tree is known. Exemplary of this type of prior art is R. J. Campana, *Proc. Amer. Phytopathol, Soc.*, 3: 266 (1976). Also, it is known that certain strains of *P. syringae* exert an antimycotic effect against *C. ulmi* when tested in vitro. This type of prior art is illustrated by D. F. Myers, D. C. Sands and G. A. Strobel, *Proc. Amer. Phytopathol. Soc.*, 12: 202 (1978).

However, this and the other prior art of which I am aware is deficient as failing to provide a method for treating Dutch elm disease that requires a single control procedure. Furthermore, this prior art fails to provide a single treatment procedure for the treatment of Dutch elm disease since retreatment is required.

DISCLOSURE OF THE INVENTION

It is accordingly one object of the present invention to provide a method for treating Dutch elm disease that requires only a single control procedure, that is, it does not require a combination of control strategies.

A further object of the present invention is to provide a method for treating Dutch elm disease that requires only a single treatment, that is, retreatment is not necessary.

Other objects and advantages of the present invention will become apparent as the description thereof proceeds.

In satisfaction of the foregoing objects and objectives, there is provided by this invention a method for treating Dutch elm disease. This method includes the step of applying to an elm tree, a Dutch elm disease-controlling amount of *P. syringae* NRRL B-12050 or any equivalent microorganism that produces an antimycotic substance or a high molecular weight antibiotic that is the same as that produced and obtained from *P. syringae* NRRL B-12050 as explained hereinafter.

The antimycotic substance is characterized as the same as that obtained by incubating *P. syringae* NRRL B-12050 at about 25°–28° C. in an about 1.5–2.5% potato dextrose broth adjusted to a final concentration of about 0.5–3% glucose, for about two to four days, and treating the incubated broth with an extracting agent to isolate the antimycotic substance therefrom.

The antibiotic is characterized as the same as that obtained by incubating *P. syringae* NRRL B-12050 at about 25°–28° C. in an about 1.5–2.5% potato dextrose broth adjusted to a final concentration of about 0.5–3% glucose, for about two to four days; mixing a precipitating agent with the inoculated broth in an amount sufficient to precipitate very high molecular weight substances from the broth; separating the precipitate and the liquid phase from each other; evaporating the liquid phase to dryness, thereby leaving a residue; chromatographing the residue on a column capable of separating in the void volume of eluate, substances having a molecular weight of a least about 1,800 from low molecular weight substances; and recovering the antibiotic from the void volume of eluate; wherein the steps for obtaining the antibiotic are carried out at a temperature below about 50° C.

Also provided by the invention is a method of treating Dutch elm disease using either the antimycotic substance or high molecular weight antibiotic. Finally, there is provided a process for obtaining the antibiotic and the antibiotic produced by the process.

The invention is particularly described herein with respect to *P. syringae* NRRL B-12050.

BEST MODE FOR CARRYING OUT THE INVENTION

My method is preferably carried out by applying to an elm tree, a Dutch elm disease-controlling amount of *P. syringae* NRRL B-12050 or equivalent microorganism. Application is preferably early in the growing season for best results, especially when the sap is active. *P. syringae* NRRL B-12050, an illustrative strain useful in this invention, is an oxidase negative, fluorescent pseudomonad that forms an antimycotic substance. This strain was obtained from David Sands of Montana State University and has been designated DC 27+ in the culture collection of Montana State University, Bozeman, Montana, U.S.A. A culture thereof has been placed on permanent unrestricted deposit with the culture collection of the Northern Utilization Research and Development Division of the U.S. Dept. of Agriculture and has been assigned Accession No. NRRL B-12050.

The *P. syringae* is maintained routinely in sterile distilled water and is re-isolatable at about 28° C. in the dark, on potato dextrose agar (PDA) plates or on medium B of E. O. King et al. in *J. Lab. Clin. Med.*, 44: 301–307 (1954), the pertinent portion of this publication being hereby incorporated by reference into this application.

The *P. syringae* is preferably applied to the elm by injection, with a sufficient amount of the *P. syringae* being in the range of about $10^8$–$10^{11}$ total cells or in the range of about $10^8$–$10^9$ living cells. Suitably, the *P. syringae* is injected in an aqueous vehicle containing nutrients such as Dye's salts supplemented with about 1% glucose. Dye's salts are disclosed in D. W. Dye, *N.Z.J.Sci.*, 6: 495–506 (1963), which is hereby incorporated by reference into this application.

One method for carrying out the injection is a gravity flow method. This method is suitable for use in smaller elm trees. In this method, the *P. syringae* in suitably about 1 liter of Dye's salts supplemented with 1% glucose, is injected into an elm by drilling four to six holes, 11 mm in diameter and 2.5 cm deep, into the base of the elm, by fitting these holes with a plastic hosing network attached to a 1 liter plastic bottle containing this 1 liter mixture, and placing the plastic bottle about 1 m above the ground. Uptake is complete when the bottle is empty, with about 12 to 36 hours being sufficient. An alternative method is pressure injection. This method is preferable for larger elm trees. A pressure of about 10 lbs. is suitable. For pressure injection, there is used about 4 to 5 times the number of *P. syringae* cells in 60 liters of water containing about 4 liters of Dye's salts supplemented with 1% glucose. This mixture is injected into the elm via 20 to 30 T's, into root flares 20 cm below the ground. Injection of the 60 liter volume takes 24 hours, with a higher pressure requiring a shorter time and a lower pressure requiring a longer time. When injection of the 60 liter solution is complete, the tree is flushed with water to ensure adequate distribution of the bacterial cells in the tree. About 24 hours is sufficient for this flushing step.

The *P. syringae* may be used either prophylactically or therapeutically to treat Dutch elm disease. Therapeutic treatment is discussed in more detail below.

The antimycotic substance of *P. syringae* NRRL B-12050 is produced in accordance with the procedure described below for producing a high molecular weight antibiotic of the *P. syringae*. In a less perferred method, the potato dextrose broth contains about 0.4% casein hydrolysate in addition to the glucose. A crude preparation of the antimycotic substance is obtained by contacting the incubated broth with an extracting agent such as n-butanol, according to the method of D. C. Gross and J. E. De Vay in *Physiol. Plant Pathol.*, 11: 13–28 (1977), which publication is hereby incorporated by reference into this application. In vitro activity against *C. ulmi* of this isolate is demonstrated by the methods set forth below in Example 1, except that five microliters of the preparation are diluted with an equal volume of water and the diluted preparation is deposited into a well (2 mm diameter×6 mm height) on the plate rather than inoculating the plate with *P. syringae.*

Treatment of Dutch elm disease with the antimycotic substance is accomplished by injecting the substance into an elm using the procedure set forth above except that the aqueous carrier does not contain the nutrients (Dye's salts and glucose). The antimycotic is injected in a Dutch elm disease-controlling amount. A disadvantage with this method for treating the disease is that retreatment may be required. However, in view of the effectiveness of this antimycotic substance, the scope of this invention covers any *P. syringae* forming this antimycotic substance, for the treatment of Dutch elm disease. The amount of the antimycotic substance injected depends upon factors such as the size of the tree.

Dialysis and thin layer chromatography (TLC) of the antimycotic substance formed by *P. syringae* Comparative Isolate 2 (see examples) and of the antimycotic substance formed by *P. syringae* NRRL B-12050 show that these two antimycotic substances are different. Specifically, this testing shows the presence of three compounds in the substance formed by *P. syringae* NRRL B-12050 and the presence of two compounds in the substance formed by *P. syringae* Comparative Isolate 2, with the additional compound in the former substance being retained by a dialysis membrane, whereas the other compounds pass through. In vitro testing of a crude isolate of this additional compound, generally using the procedure of Example 1 below, shows activity against *C. ulmi* and thus that the substance is antifungal. In vitro testing of a crude isolate of the other two compounds in combination, and of a crude isolate of the material formed by *P. syringae* Comparative Isolate 2 in combination, also shows activity against *C. ulmi.*

Comparison of the TLC of the former substance against the TLC of the antimycotic substance formed by De Vay's B-3 strain of *P. syringae* shows by $R_f$ values that the components of the substances are completely different. This difference may explain the apparent lack of phytotoxicity of *P. syringae* NRRL B-12050 in the elm, which is clearly shown by examination of the xylem cylinder in the Example 5 control, in which there is not inoculation with *C. ulmi.*

*P. syringae* NRRL B-12050 forms a high molecular weight antibiotic. The antibiotic is produced by incubating the microorganism at about 25°–28° C. in an about 1.5–2.5% potato dextrose broth (Difco) adjusted to a final concentration of about 0.5–3% glucose, for about two to four days. Preferably, about 2% potato dextrose broth and about 1% glucose are used, and the incubation time is about three days at about 27° C. Athough the microorganism may be incubated in standing culture, it is preferred to increase the available oxygen by either shaking the culture or oxygenating using a conventional bubbler. Conveniently, the culture, is shaken constantly using conventional apparatus. Production of the antibiotic is particularly enhanced by including in the broth about 10 millimolar ferric chloride and about 2.3 g/l histidine. Other amino acids such as ornithine that stimulate the antibiotic production, may be used in place of histidine. These amino acids may be included in the aqueous vehicle when the *P. syringae* is injected. A useful amount of ferric chloride ranges from about 5–20 millimolar, and a useful quantity of histidine ranges from about half, up to about two to three times the amount of histidine just described.

The high molecular weight antibiotic is recovered from the incubated broth in the following way. A precipitating agent is mixed with the broth in an amount sufficient to precipitate very high molecular weight substances. By "very high molecular weight" is meant a molecular weight of at least from about 15,000-20,000. Acetone is used with particular advantage as the precipitating agent, with about two volumes of acetone being suitable for mixing with about one volume of broth. The precipitate and the liquid phase are then separated from each other by a conventional procedure such as filtration, the precipitate is discarded, and the liquid phase is evaporated to dryness, leaving a residue. The temperature in the processing steps is maintained below about 50° C. to ensure that decomposition of the antibiotic does not occur.

The residue is chromatographed on a column capable of separating in the void volume of eluate, substances having a molecular weight of at least about 1,800 from low molecular weight substances. By "low molecular weight" is meant a molecular weight of less than about 1,800. The chromatography is suitably at atmospheric pressure using gravity flow. Chromatography is advantageously carried out using an aqueous solvent such as water as the eluent, and an about 90 cm × 1.5 cm column packed with acrylamide beads such as those known as Biogel P-2, available from Biorad. The residue is placed on the column after being dissolved in a minimal amount of the eluent, and the high molecular weight antibiotic is obtained in the void volume of eluate.

The antibiotic is crystalline and is recovered from the eluate as crystals by a conventional procedure. Conveniently, crystals are obtained by allowing the eluate to stand. Analysis of the crystals shows that the antibiotic consists of amino acids. These amino acids are arginine, unknown amino acid, aspartic acid, threonine, serine, glutamine, glycine, alanine, valine, methionine, isoleucine, leucine, tyrosine, and phenylalanine. The relative molar ratios of the amino acids are unknown, but from the chromatography work described above, it is known that the antibiotic has a molecular weight between about 1,800 and 15,000-20,000. Although the antibiotic is retained during ultrafiltration by a PM-10 membrane, which has a nominal molecular weight cutoff of 10,000, and which is available from Amicon, the antibiotic may have a molecular weight less than 10,000 since affinity for the membrane could be responsible for retention. The antibiotic does not enter a native 15% polyacrylamide gel.

Bioactivity of the antibiotic crystals is verified by redissolving the crystals, spotting the resulting solution on an agar plate, and overspraying with C. ulmi (spot test). Using a similar testing procedure, the supernatant remaining after crystal formation, is found to be inactive.

The antibiotic is acetone soluble, fairly water soluble, heat stable, sensitive to base above pH of about 7.5 to 8, acid stable at pH no lower than about 4 to 5, insensitive to proteinase K, and refractory to leucine aminopeptidase inactivation. Heat stability is shown by boiling for three minutes followed by the spot test. The effect of base is shown by 1 N sodium hydroxide treatment followed by neutralization and the spot test. Insensitivity to proteinase K is demonstrated by 30 minute treatment followed by the spot test. The antibiotic is similarly shown to be refractory to leucine aminopeptidase inactivation.

Production of the antibiotic is stimulated by the addition of histidine or ornithine. This has been shown in Dye's medium containing about 1% glucose. Production is repressed by the addition of glutamate or asparagine, or by the addition of casamino acids. This has also been found using Dye's medium. The addition of about 10 ppm ferric chloride overcomes the repression of casamino acids. The antibiotic has been reproducibly isolated from broth culture using the procedure described earlier, and from Dye's medium to which histidine and ferric chloride have been added, but has not been reproducibly isolated from Dye's medium to which casamino acids and ferric chloride have been added, nor from Dye's medium to which only histidine has been added.

Treatment of Dutch elm disease with the high molecular weight antibiotic may be achieved by injecting the antibiotic into an elm using the procedure set forth above for the microorganism, except that it is not necessary for the aqueous carrier to contain the nutrients (Dye's salts and glucose). Retreatment may be required with this method, and thus this method is less preferred than a method using an appropriate strain of *P. syringae.* The antibiotic is injected in an amount sufficient to control Dutch elm disease. Since it is this material that clearly appears to enable *P. syringae* NRRL B-12050 to control Dutch elm disease, the scope of this invention covers the use of any *P. syringae* forming this high molecular weight antibiotic, for the treatment of Dutch elm disease. Additionally, since using recombinant DNA techniques, microorganisms other than *P. syringae* may be prepared that will produce this high molecular weight antibiotic, such genetically engineered microorganisms are equivalent to this *P. syringae,* for purposes of this invention. The high molecular weight antibiotic is a component of the antimycotic substance discussed above.

The below examples are illustrative of the method of the present invention and illustrate the unpredictability associated with my discovery of a type of *P. syringae* that is useful against Dutch elm disease. It was unexpectedly discovered in carrying out this work that the *P. syringae* does not appear to have a phytotoxic effect on the elm. In view of the work of De Vay, for example, U.S. Pat. No. 3,155,585, the likelihood existed that any strain of *P. syringae* found effective against Dutch elm disease would be phytotoxic. The present invention provides a most advantageous method for treating Dutch elm disease since *P. syringae* is capable of living in the elm. Thus, a one treatment procedure is made possible since the microorganism is viable within the tree and exerts a Dutch elm disease controlling effect during the period of viability.

EXAMPLE 1

*P. syringae* NRRL B-12050, an antimycotic substance-forming bacterium, is tested by the following procedure for in vitro activity against *C. ulmi* isolate UT-5F, obtained from N. K. Van Alfen of Utah State University. A 5 microliter sample of the *P. syringae* is taken from a liquid culture containing about $1\times10^8$ colony forming units/ml and is deposited aseptically by loop inoculation on Dye's glucose agar (DGA). DGA plating medium is a modified mineral-salts medium in which 1% glucose is the carbon source and in which Noble agar (1.2%) (Difco) is used. The inoculated plate is incubated at 28° C. in the dark for 27 hours. There is then sprayed onto the surface of the plate using a 3 second spray, an aqueous suspension of the *C. ulmi* having a concentration of $5 \times 10^6$ spores/ml. A gas-propelled sprayer is used and the sprayer is held about 30 mm from the plate. After the sprayed plate is incubated at room temperature for 2 days, the activity of the *P. syringae* against the *C. ulmi* is determined by the area of the clear inhibition zone surrounding the *P. syringae* colony. The area of the clear inhibition zone is 216 mm² for the *P. syringae*.

EXAMPLE 2

Following the procedure of Example 1 except that a potato dextrose agar (PDA) plate is used instead of the DGA plating medium, there is found to be a clear inhibition zone having an area of 204 mm².

COMPARATIVE EXAMPLE 1

Following the procedure of Example 1 except that *P. syringae* Comparative Isolate 1 is used instead of *P. syringae* NRRL B-12050, there is obtained a clear inhibition zone having an area of 0 m². This strain of *P. syringae* is designated DC 27- in the Montana State University collection and differs from *P. syringae* NRRL B-12050 only in that it does not form any antimycotic substance.

COMPARATIVE EXAMPLE 2

Following the procedure of Example 1 except that *P. syringae* Comparative Isolate 2 is used rather than *P. syringae* NRRL B-12050, there is obtained a clear inhibition zone having an area of 452 mm². This strain of *P. syringae* is designated DC 323+ in the Montana State University collection and forms an antimycotic substance.

EXAMPLE 3

The in vitro activity of *P. syringae* NRRL B-12050 against *C. ulmi* UT-5F on a medium containing elm wood extract is determined by following the procedure set forth in Example 1 except that an elm wood extract-containing medium is used instead of the DGA plating medium. The extract-containing medium is prepared as follows. Elm twigs are harvested from the current year's growth of mature elms, the leaves are excised, and the twigs are cut into 2–5 cm segments. The twig segments are homogenized with an "omni-Mixer" (Sorvall) for 2 minutes in distilled water in the proportion of 1 part twigs (fresh weight in grams) to 5 parts water (ml). The extract is filtered through two layers of cheesecloth and is centrifuged at 4° C. for 20 minutes at 4,000 g. The pellet is discarded. The supernatant [11.3 mg (dry weight)/ml] is sterilized, is diluted with distilled water at 4.0, 6.0, 12.5, 20.0 and 100% (vol/vol) and is incorporated into agar (Sigma, 1.3%), pH 7.1. The results are set forth in Table 1. Antimycotic production is calculated in this table and in Table 2 using the equation $y = a + b \ln X$, where y is the area of the zone of inhibition (mm²), X is the concentration of antimycotic (mg/ml), and a and b are constants with values dependent in part upon the type and thickness of the agar.

COMPARATIVE EXAMPLE 3

Following the procedure of Example 3 except that *P. syringae* Comparative Isolate 2 is used rather than *P. syringae* NRRL B-12050, the results set forth in Table 1 are obtained.

TABLE 1

| P. syringae isolate | Activity against *C. ulmi* on medium containing elm wood extract (units)* dilution of original elm wood extract | | | | |
|---|---|---|---|---|---|
| | $\frac{1}{3}$ | $\frac{1}{6}$ | $\frac{1}{12.5}$ | $\frac{1}{20}$ | $\frac{1}{100}$ |
| NRRL-B-12050 | 7.1 | 7.1 | 0 | 0.8 | 0 |
| Comparative Isolate 2 | 19.6 | 3.1 | 3.1 | 7.1 | 0 |

*One unit of antimycotic activity is defined as that amount of antimycotic which produces a 1 mm² zone of inhibition in a bioassay against *C. ulmi* (UT-5F).

TABLE 2

| P. syringae isolate | Activity against *C. ulmi* on medium containing expressed elm sap (units) Concentration % | | | | |
|---|---|---|---|---|---|
| | 0 | 0.01++ | 0.05 | 0.1 | 1.0 |
| NRRL-B-12050 | 0 | 0.8 | 0.8 | 3.1 | 3.1 |
| Comparative Isolate 2 | 0.2 | 4.9 | 15.9 | 9.6 | 4.9 |

++The concentration of sap that most closely approximates its concentration in elm.

EXAMPLE 4

The in vitro activity of *P. syringae* NRRL B-12050 against *C. ulmi* UT-5F on a medium containing expressed cell sap is determined by following the procedure set forth in Example 1 except that an expressed sap-containing medium is used rather that the DGA plating medium. The expressed elm sap-containing medium is prepared by expressing sap from cuttings of new growth from mature elm trees with a plant water status console (Model 3005, Soilmoisture Equipment Corp.). Fluid passing through the stems equal to the volume of the stem is collected with an instrument reading of 5–10 bars, is concentrated about ten times by flash evaporation at 35° C., is freeze dried, and the resulting powder is dried over $P_2O_5$. This powder is then incorporated into a solid medium (1.2% Noble agar, Difco) at 0.01, 0.05, 0.1 and 1.0% (w/v). The results are set forth in Table 2. These results and those in Table 1 show that elm wood extract and expressed xylem sap support the growth of *P. syringae* NRRL B-12050.

COMPARATIVE EXAMPLE 4

Following the procedure of Example 4 except that *P. syringae* Comparative Isolate 2 is used instead of *P. syringae* NRRL B-12050, the results set forth in Table 2 are obtained.

EXAMPLE 5

(A) The effectiveness of *P. syringae* NRRL B-12050 as a protectant against Dutch elm disease is studied in the greenhouse using elm seedlings having a height of about 1.5–2.0 m. Each of eight trees is injected in mid-spring by gravity flow with $5 \times 10^8$ cells/ml of the *P. syringae*, in 60 ml of distilled water containing 1% w/v glucose. The injection is achieved by allowing the cell suspension to flow from an inverted 60 ml plastic bottle suspended about 1 m above the soil level in the pot and containing the cell suspension, into a hole (0.44 cm in diameter) drilled into a tree internode about 20 cm above the soil line. The connection between the tree and bottle is made by fitting the hole with a plastic tubing adapter that is sealed to the tree with silicone rubber adhesive, and inserting one end of a rubber tubing (3 mm inner diameter) into this adapter and the other end into a plastic tubing adapter fitted onto the bottle. Two weeks after injection with the *P. syringae*, each tree is massively challenged with 1 ml of a suspension of an isolate of *C. ulmi* ($10^4$ spores/ml). In order to inject the *C. ulmi*, a rectangular area of bark (5–10×20–25 mm) about 10 cm above the site inoculated with the *P. syringae* is cut on three sides, the resulting bark patch is peeled back to reveal the xylem, and the exposed xylem is flooded with the *C. ulmi*. Afterwards, the bark patch is replaced, and the inoculation site is wrapped with masking tape and then aluminum foil to reduce desiccation.

Eight to ten weeks after inoculation with the *C. ulmi*, each tree is rated for disease symptoms including wilt and vascular discoloration, the latter being determined as a percentage of the length of the stem xylem discolored. The results are set forth in Table 3.

(B) As a control, the above procedure is followed for 11 more elm trees, except that only *C. ulmi* is injected. Xylem discoloration is used as an estimate of pathogen development since it occurs in 100% of these inoculated trees and is associated closely with the extent of pathogen development in Dutch elm disease. The results are set forth in Table 3.

TABLE 3

| Treatment | Number of Trees | Mean % Discoloration (individual trees)+ | Number of Trees Expressing Wilt or Yellowing |
|---|---|---|---|
| *P. syringae* NRRL B-12050 and *C. ulmi* | 8 | $2^x$ (0,0,0,0,0,3, 4,6) | 0 |
| *P. syringae* Comparative Isolate 1 and *C. ulmi* | 14 | $41^y$ (0,0,2,8,10, 11,38,50,56, 51,82,83,86,89) | 7 |
| *P. syringae* Comparative Isolate 2 and *C. ulmi* | 11 | $21^x$ (0,3,3,7,10,13, 14,25,27,30,100) | 1 |
| *P. syringae* Comparative Isolate 3 and *C. ulmi* | 10 | $67^y$ (8,29,36,41,67, 91,100,100,100 100) | 2 |
| *P. syringae* NRRL B-12050 | 6 | $0^x$ (0,0,0,0,0,0) | 0 |
| *P. syringae* Comparative Isolate 2 | 5 | $10^x$ (3,8,12,13,7) | 0 |
| *C. ulmi* (control) | 11 | $54^y$ (7,9,23,45,47, 60,60,67,74,100, 100) | 8 |

+Values followed by the same letter are not significantly different (P = 0.05) according to the Newman-Keuls Test.

(C) As a further control, the above procedure used for *P. syringae* NRRL B-12050 is followed for six more elm trees, except that injection of the *P. syringae* is not followed by challenge with *C. ulmi*. Table 3 shows the results. The lack of discoloration shows that this strain is not phytotoxic.

COMPARATIVE EXAMPLE 5

(A) Following the procedure of Example 5(A) except that *P. syringae* Comparative Isolate 1 is used rather than *P. syringae* NRRL B-12050, and using 14 more elm trees, the results set forth in Table 3 are obtained. *P. syringae* Comparative Isolate 1 differs from *P. syringae* NRRL B-12050 only in that it does not form an atimycotic substance.

(B) Following the procedure of Example 5(A) except that *P. syringae* Comparative Isolate 2 is used rather than *P. syringae* NRRL B-12050, and using 11 more elm trees, the results set forth in Table 3 are obtained. Cells from two-day-old cultures of this isolate are used.

As a control, the procedure set forth in the above paragraph is followed for five more elm trees, except that the elms are not challenged with *C. ulmi*. The presence of 10% mean xylem discoloration suggests that this strain of *P. syringae* is phytotoxic. In contrast, as shown by Example 5(C), *P. syringae* NRRL B-12050 is not phytotoxic. The apparent lack of phytotoxicity for this strain is unexpected in view of the prior work of De Vay, for example, U.S. Pat. No. 3,155,585. This work discloses that the more virulent or phytotoxic an isolate of *P. syringae* is, the more antibiotic or more antifungal it is. Thus, the likelihood existed that even if one could find a strain of *P. syringae* useful for treating Dutch elm disease, the strain would be phytotoxic and consequently not useful. Contrary to this expectation in the prior art, this data shows a type of *P. syringae* in which antifungal activity and efficacy in treating Dutch elm disease are not related to phytotoxicity.

(C) Following the procedure of Example 5(A) except that *P. syringae* Comparative Isolate 3 is used rather than *P. syringae* NRRL B-12050, and using 10 more elm trees, the results set forth in Table 3 are obtained. Cells from two-day-old cultures of this isolate are used in this treatment. Comparative Isolate 3 differs from Comparative Isolate 2 only in that it does not form an antimycotic substance.

To determine the relative development of *P. syringae* NRRL B-12050, *P. syringae* Comparative Isolate 2 and *C. ulmi* in the trees of Example 5 and Comparative Example 5, each tree stem is cut into 2–3 cm pieces, cut in half longitudinally, and the bark removed. One piece is inoculated on a *P. syringae* selective medium, and the other piece on a *C. ulmi* selective medium. The xylem of all trees treated with *P. syringae* Comparative Isolate 2 is discolored at the point of injection up to 10 cm from that internode. No symptoms of phytotoxicity are observed on the leaves, petioles, or stems of the trees treated with either *P. syringae* strain.

P. syringae is isolated from under the bark from 90% of the sites injected with *P. syringae* NRRL B-12050. *P. syringae* Comparative Isolate 2 moved an average of 21 cm (range 0-64) from the injection point, and *P. syringae* NRRL B-12050 moved an average of 8 cm (range 0-12) from the injection point.

As can be seen from this data, injection of the elms at the beginning of the second growth period (mid-spring) with either *P. syringae* NRRL B-12050 or *P. syringae* Comparative Isolate 2 significantly suppresses vascular discoloration due to *C. ulmi*, when compared with trees injected with isolates not producing antimycotics or injected with *C. ulmi* alone.

Additional work with greenhouse elms shows that application of *P. syringae* to the elms at the end of the second growth period (mid-summer) does not protect them from Dutch elm disease.

EXAMPLE 6

A limited study of the effectiveness of *P. syringae* NRRL B-12050 as a protectant against Dutch elm disease is conducted in sapling elms, 6 m in height and 7–10 cm in diameter, in a field plot located near Washington, D.C. In late spring, each of three trees in the plot is inoculated by gravity flow with approximately $10^{11}$ cells of the *P. syringae*, in one liter of Dye's salts supplemented with 1% glucose. The inoculation is accomplished by drilling four to six holes 11 mm in diameter and 2.5 cm deep, into the base of each tree and fitting the holes with a plastic hosing network attached to a one-liter plastic bottle positioned 1 m above the ground and containing the cell suspension. The inoculation is complete within 12–36 hours. About two weeks later, each tree is massively challenged with a mixture of two aggressive isolates of *C. ulmi* (UT-5F and one isolate from Washington, D.C.) by flooding 4–8 chisel wound made in the main branches of each tree with $5 \times 10^4$ spores of the *C. ulmi*, and subsequently covering the wounds with clear plastic tape. At the end of the second growing season, each tree is scored for disease symptoms based on the percent of the crown noticeably affected by Dutch elm disease. Of the three trees, one is found to be free of symptoms, and the two others are found to have died. This experiment is repeated with two or more trees, and at the end of the growing season one year later, one tree is found to show 1% crown symptoms and the other is found to have died.

As a control, the procedure set forth in the above paragraph is followed in several trees except that only *C. ulmi* is injected. All control trees are found to develop symptoms of Dutch elm disease and to die.

The procedure set forth in the first paragraph of this example is repeated except that the *P. syringae* inoculation is in mid-summer. The fungus is injected in early September. Each tree is found to develop Dutch elm disease the following year and to die. Experimentation using pressure injection of 30 psi, rather than gravity flow, is tried but found also ineffective in conferring protection to the elms.

COMPARATIVE EXAMPLE 6

Following the procedure of Example 6 (using late spring injection), except that *P. syringae* Comparative Isolate 2 is used rather than *P. syringae* NRRL B-12050, and using four more elm trees in the plot, observation at the end of the second growing season shows that all trees died. This experiment is repeated with five more trees, and at the end of the growing season one year later, two trees show no symptoms and the other three trees have died. Examination of the xylem wood beneath the bark of the living trees shows vast discoloration and thus *C. ulmi* development. It is therefore expected that these trees will also succumb to Dutch elm disease the following year.

EXAMPLE 7

The therapeutic effect of *P. syringae* NRRL B-12050 against Dutch elm disease is tested in the field as follows. Twenty elms in Sioux Falls, S. Dak. 36-77 cm in diameter (1.5 m), and two elms in Missoula, Mont. showing symptoms of natural infection of Dutch elm disease, are each inoculated with about $5\times10^{11}$ cells of the *P. syringae* in 60 l of water containing four liters of Dye's salts supplemented with 1% glucose. Each tree is verified as having Dutch elm disease by growth of *C. ulmi* on the selective medium of R. V. Miller et al, *Plant Disease* (in press, 1980), or a positive immunochemical reaction. Testing of the latter type is described in J. Nordin et al, *Plant Physiology* (in press, 1980). The inoculation is accomplished via 20-30 T's attached to a hosing network and inserted into the root flares 20 cm below the ground, with the injection being carried out at 10 psi for 24 hours, followed by flushing each tree with water for 24 hours to ensure adequate distribution of the bacteria within the tree. A total of 22 trees is injected, and each tree is evaluated for the extent of crown symptoms by estimates made from grid diagrams or photographs made of each tree. The estimates are made at the time of treatment, and at the beginning and end of the second growing season. Dead branches appearing in the trees at the end of the first growing season are not removed. The results are shown in Table 4.

Trees of the same relative size that show virtually the same degree of disease severity are used as matched controls. The results for the control trees are shown in Table 4.

The Table 4 data shows that treatment should be carried out in the earlier part of the growing season, and that the crown should be at least about 90% healthy when treatment is initiated. Six out of seven trees treated in the earlier part of the growing season and having at least 90% of the crown apparently healthy show no worsening of the disease at the end of the second growing season; whereas, only one out of nine of the control trees treated during the same period and having at least 90% of the crown apparently healthy is found to have resisted further spread of the disease.

TABLE 4

Theraputic treatment of diseased elms in the field*

| Tree | Date of Treatment | Proportion of crown apparently healthy at beginning of test % | Proportion of crown apparently healthy at beginning of second season (5/20) % | Proportion of crown remaining at end of second season (9/1) % |
|---|---|---|---|---|
| Treated-1 | 6/14 | 90 | 90 | 90 |
| Control-1 | | 90 | 0 | 0 |
| Treated-2 | 6/19 | 70 | 0 | 0 |
| Control-2 | | 80 | 0 | 0 |
| Treated-3 | 6/21 | 80 | 60 | 0 |
| Control-3 | | 70 | 0 | 0 |
| Treated-4 | 6/21 | 90 | 90 | 85 |
| Control-4 | | 80 | 0 | 0 |
| Treated-5 | 6/22 | 80 | 0 | 0 |
| Control-5 | | 90 | 10 | 0 |
| Treated-6 | 6/25 | 90 | 50 | 0 |
| Control-6 | | 90 | 40 | 0 |
| Treated-7 | 6/29 | 80 | 50 | 0 |
| Control-7 | | 80 | 30 | 0 |
| Treated-8 | 6/29 | 95 | 95 | 95 |
| Control-8 | | 90 | 10 | 0 |
| Treated-9 | 7/2 | 70 | 0 | 0 |
| Control-9 | | 90 | 0 | 0 |
| Treated-10 | 7/2 | 80 | 80 | 60 |
| Control-10 | | 90 | 10 | 0 |
| Treated-11 | 7/5 | 95 | 95 | 95 |
| Control-11 | | 95 | 95 | 95 |
| Treated-12 | 7/9 | 90 | 80 | 40 |
| Control-12 | | 80 | 50 | 0 |
| Treated-13 | 7/9 | 80 | 50 | 0 |
| Control-13 | | 80 | 0 | 0 |
| Treated-14 | 7/10 | 90 | 70 | 0 |
| Control-14 | | 80 | 20 | 0 |
| Treated-15 | 7/11 | 80 | 50 | 0 |
| Control-15 | | 80 | 50 | 0 |
| Treated-16 | 7/16 | 90 | 90 | 0 |
| Control-16 | | 90 | 80 | 0 |
| Treated-17 | 7/18 | 80 | 0 | 0 |
| Control-17 | | 80 | 80 | 0 |
| Treated-18 | 7/19 | 90 | 0 | 0 |
| Control-18 | | 80 | 0 | 0 |
| Treated-19 | 7/20 | 80 | 80 | 0 |
| Control-19 | | 90 | 80 | 0 |
| Treated-20 | 7/24 | 90 | 90 | 0 |
| Control-20 | | 80 | 10 | 0 |
| +Treated-21 | 8/2 | 90 | 90 | 90 |
| +Control-21 | | 90 | 80 | 50 |
| +Treated-22 | 8/2 | 90 | 90 | 90 |

TABLE 4-continued Theraputic treatment of diseased elms in the field*

| Tree | Date of Treatment | Proportion of crown apparently healthy at beginning of test % | Proportion of crown apparently healthy at beginning of second season (5/20) % | Proportion of crown remaining at end of second season (9/1) % |
|---|---|---|---|---|
| +Control-22 | | 90 | 80 | 40 |

*The means of treatment and control groups at the second and final readings were significantly different at the 1% level.
+These trees are located in Missoula, MT. These trees are about 3 weeks behind in growth and development when compared to those in Sioux Falls, SD.

The greenhouse data and the Washington D.C. field data, in which the *P. syringae* is used prophylactically, show that it is best to inject the *P. syringae* early in the growing season, such as in midspring. The optimum time is when the sap is flowing up the tree and maximum early transpiration is taking place. Thus, in carrying out this invention, treatment should be early in the growing season, for the microorganism or for the active component produced by the microorganism.

In all but one of the *P. syringae*-treated trees, fluorescent antimycotic-producing pseudomonads are recovered readily from trunk borings during the spring of the second season and from branches sampled in at least three different sites from the crowns of trees surviving two growing seasons. This demonstrates the ability of the *P. syringae* to live in the tree and to survive through winter. *P. syringae* is not recovered from the crowns of treated trees that succumb to Dutch elm disease.

EXAMPLE 8

The high molecular weight antibiotic of *P. syringae* NRRL B-12050 is produced by incubating the microorganism at 27° C. for three days in 2% potato dextrose broth containing 1% glucose, 10 millimolar ferric chloride, and 2.33 g/l histidine. The culture is constantly shaken during the incubation. The high molecular weight antibiotic is recovered from the broth by adding two volumes of acetone to one volume of broth, separating the precipitate and the liquid phase from each other by filtration, evaporating the filtrate and subjecting the residue to column chromatography. Chromatography is carried out at atmospheric pressure using gravity flow. These processing steps are carried out at a temperature below about 50% to ensure that decomposition of the antibiotic does not occur.

Chromatography is carried out using water as the eluent, and a 90 cm×1.5 cm column packed with Biogel P-2 beads, available from Biorad. The residue is placed on the column after being dissolved in minimal amount of water, and the high molecular weight antibiotic is obtained in the void volume of eluate.

The eluate is allowed to stand overnight to produce crystals of the high molecular weight antibiotic. Analysis of the crystals shows that the antibiotic consists of amino acids. Data pertaining to this antibiotic are set forth above in the description preceding the examples.

EXAMPLE 9

The antimycotic substance of *P. syringae* NRRL B-12050 is obtained by incubating the *P. syringae* in a potato dextrose broth (Difco) containing 0.4% casein hydrolysate (Sigma) and adjusted to a final concentration of 1.5% glucose. The incubation is carried out at 27° C. for three days in standing culture. One liter of the incubated cell suspension is extracted with n-butanol, the n-butanol is removed by evaporation, and one-twentieth of the residue is dissolved in 5–10 ml water. The resulting aqueous mixture is injected into one limb (1–1.5 cm in diameter) of an elm tree. Afterwards, the limb is challenged with *C. ulmi.* The limb is observed to be free of symptoms of Dutch elm disease about one year later.

APPLICABILITY

This invention is used for the control of Dutch elm disease.

I claim:

1. A method for treating Dutch elm disease comprising applying a high molecular weight antibiotic-forming strain of *P. syringae* to an elm tree in a Dutch elm disease-controlling amount; said antibiotic being the same as that obtained by incubating *P. syringae* NRRL B-12050 at about 25°–28° C. in an about 1.5–2.5% potato dextrose broth adjusted to a final concentration of about 0.5–3% glucose, for about two to four days; mixing a precipitating agent with the inoculated broth in an amount sufficient to precipitate very high molecular weight substances from said broth; separating the precipitate and the liquid phase from each other; evaporating the liquid phase to dryness, thereby leaving a residue; chromatographing the residue on a column capable of separating in the void volume of eluate substances having a molecular weight of at least about 1,800 from low molecular weight substances; and recovering said antibiotic from said void volume of eluate; wherein the steps for obtaining said antibiotic are carried out at a temperature below about 50° C.

2. The method of claim 1, wherein said high molecular weight antibiotic-forming strain is an antimycotic substance-forming strain of *P. syringae;* said antimycotic substance being the same as that obtained by incubating *P. syringae* NRRL B-12050 at about 25°–28° C. in an about 1.5–2.5% potato dextrose broth adjusted to a final concentration of about 0.5–3% glucose, for about two to four days, and treating the incubated broth with an extracting agent to isolate said antimycotic substance therefrom; wherein said applying is early in the growing season.

3. A method for treating Dutch elm disease comprising applying early in the growing season, a Dutch elm disease-controlling amount of *P. syringae* NRRL B-12050 to an elm tree.

4. The method of claim 1, wherein the elm tree is treated prophylactically.

5. The method of claim 1, wherein the elm tree is treated therapeutically.

6. The method of claim 5, wherein the elm tree has at least about 90% of its crown free from Dutch elm disease.

7. The method of claim 1, wherein said applying is early in the growing season.

8. The method of claim 1 or 3, wherein said applying is by injection into the elm tree.

9. The method of claim 8, wherein said amount is in the range of about $10^8$–$10^{11}$ total cells.

10. The method of claim 8, wherein said amount is about $10^8$–$10^9$ living cells.

11. The method of claim 8, wherein the *P. syringae* is injected in an aqueous vehicle containing nutrients for the *P. syringae.*

12. The method of claim 11, wherein the aqueous vehicle further comprises an amino acid that stimulates production of said antibiotic in the elm tree.

13. The method of claim 8, wherein the injection is by gravity flow.

14. The method of claim 8, wherein the injection is at a pressure in excess of the force of gravity.

15. The method of claim 14, comprising the further step of flushing the elm with water after the injection step, whereby adequate distribution of the *P. syringae* within the tree is provided.

16. The method of claim 3, wherein the elm tree is treated prophylactically; wherein said applying is by injection into the elm tree; and wherein the *P. syringae* is injected in an aqueous vehicle containing nutrients for the *P. syringae*.

17. The method of claim 3, wherein the elm tree is treated therapeutically, the elm tree having at least about 90% of its crown free from Dutch elm disease; wherein said applying is by injection into the elm tree; and wherein the *P. syringae* is injected in an aqueous vehicle containing nutrients for the *P. syringae*.

18. A method of treating Dutch elm disease comprising injecting an elm tree with a Dutch elm disease-controlling amount of an antimycotic substance obtained by incubating *P. syringae* NRRL B-12050 at about 25°–28° C. in about 1.5–2.5% potato dextrose broth adjusted to a final concentration of about 0.5–3% glucose, for about two to four days, and treating the incubated broth with an extracting agent to isolate said antimycotic substance therefrom.

19. A method for treating Dutch elm disease comprising injecting an elm tree with a Dutch elm disease-controlling amount of the high molecular weight antibiotic produced by incubating *P. syringae* NRRL B-12050 at about 25°–28° C. in an about 1.5–2.5% potato dextrose broth adjusted to a final concentration of about 0.5–3% glucose, for about two to four days; mixing a precipitating agent with the incubated broth in an amount sufficient to precipitate very high molecular weight substances; separating the precipitate and the liquid phase from each other; evaporating the liquid phase to dryness, thereby leaving a residue; chromatographing the residue on a column capable of separating in the void volume of eluate, substances having a molecular weight of at least about 1,800 from low molecular weight substances; and recovering said high molecular weight antibiotic from said void volume of eluate; wherein the processing steps are carried out at a temperature below about 50° C.

20. The method of claim 18, wherein said injecting is early in the growing season.

* * * * *